(12) United States Patent
Ainger et al.

(10) Patent No.: US 11,382,844 B2
(45) Date of Patent: Jul. 12, 2022

(54) SHAMPOO COMPOSITION AND METHOD OF USE

(71) Applicant: Conopco, Inc., Englewood Cliffs, NJ (US)

(72) Inventors: Nicholas John Ainger, Wirral (GB); Wei Gao, Fort Washington, PA (US); Adam Peter Jarvis, Liverpool (GB); Kinjalbahen Joshi, Collegeville, PA (US); Curtis Schwartz, Ambler, PA (US); Neil Scott Shaw, Warrington (GB); Inna Shulman, Langhorne, MI (US); Pierre Starck, Chester (GB); Sally Elizabeth Wood, Warrington (GB); Fanwen Zeng, Audubon, PA (US)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 16/761,065

(22) PCT Filed: Oct. 19, 2018

(86) PCT No.: PCT/EP2018/078743
§ 371 (c)(1),
(2) Date: May 1, 2020

(87) PCT Pub. No.: WO2019/086276
PCT Pub. Date: May 9, 2019

(65) Prior Publication Data
US 2020/0281824 A1  Sep. 10, 2020

Related U.S. Application Data

(60) Provisional application No. 62/581,135, filed on Nov. 3, 2017.

(30) Foreign Application Priority Data

Feb. 7, 2018 (EP) .................................. 18155489

(51) Int. Cl.
| | |
|---|---|
| *A61K 8/06* | (2006.01) |
| *A61K 8/25* | (2006.01) |
| *A61K 8/29* | (2006.01) |
| *A61K 8/46* | (2006.01) |
| *A61K 8/81* | (2006.01) |
| *A61K 8/891* | (2006.01) |
| *A61K 8/898* | (2006.01) |
| *A61Q 5/02* | (2006.01) |

(52) U.S. Cl.
CPC .............. *A61K 8/06* (2013.01); *A61K 8/25* (2013.01); *A61K 8/29* (2013.01); *A61K 8/463* (2013.01);
(Continued)

(58) Field of Classification Search
None
See application file for complete search history.

(56) References Cited

U.S. PATENT DOCUMENTS

| 4,298,494 A | 3/1981 | Parslow |
| 5,154,847 A | 10/1992 | LaPetina et al. |

(Continued)

FOREIGN PATENT DOCUMENTS

| EP | 0896027 | 2/1999 |
| EP | 0995791 | 4/2000 |

(Continued)

OTHER PUBLICATIONS

Search Report and Written Opinion in EP18155491; dated Jun. 18, 2018.

(Continued)

*Primary Examiner* — Robert A Wax
*Assistant Examiner* — Quanglong N Truong
(74) *Attorney, Agent, or Firm* — Foley & Lardner LLP

(57) ABSTRACT

An acidic aqueous shampoo composition, which comprises: (I) a cleansing surfactant selected from the group consisting of anionic surfactant, zwitterionic or amphoteric surfactant and nonionic surfactant; (II) an emulsified silicone, (III) an anti-settling, thickening polymer, wherein the anti-settling, thickening polymer, comprises: (a) 40 to 74.5 wt % of structural units of $C_{1-4}$ alkyl acrylate; (b) 20 to 50 wt % of structural units of methacrylic acid; (c) 0.3 to <5 wt % of structural units of 2-acrylamido-2-methyl-propane sulfonic acid (AMPS); (d) 5 to 25 wt % of structural units of a specialized associated monomer having the following structure: wherein $R^1$ is a linear saturated $C_{10-24}$ alkyl group; wherein $R^2$ is a hydrogen or a methyl group (preferably, wherein $R^2$ is a methyl group); and wherein n is an average of 20 to 28; with the proviso that the structural units of the specialized associated monomer (d) are derived from one of (i) a single specialized associated monomer (preferably, a single specialized associated monomer wherein $R^1$ is selected from the group consisting of a linear saturated $C_{12}$ alkyl group, a linear saturated $C_{18}$ alkyl group and a linear saturated $C_{22}$ alkyl group; more preferably, a single specialized associated monomer wherein $R^1$ is selected from the group consisting of a linear saturated $C_{12}$ alkyl group and a linear saturated $C_{18}$ alkyl group); (ii) two specialized associated monomers, wherein $R^1$ is, respectively, a linear saturated $C_{12}$ and a linear saturated $C_{18}$ alkyl group; or (iii) two specialized associated monomers, wherein $R^1$ is, respectively, a linear saturated $C_{18}$ alkyl group and a linear saturated $C_{22}$ alkyl group; (f) 0 to 2 wt % of structural units of multi-ethylenically unsaturated crosslinking monomer or chain transfer agent; and wherein the sum of the weight percentages of structural units (a)-(f) is equal to 100 wt % of the anti-settling, thickening polymer; and method of treating hair or scalp with such a composition.

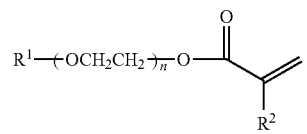

20 Claims, No Drawings

(52) U.S. Cl.
CPC .......... *A61K 8/8147* (2013.01); *A61K 8/8152* (2013.01); *A61K 8/8158* (2013.01); *A61K 8/8188* (2013.01); *A61K 8/8194* (2013.01); *A61K 8/891* (2013.01); *A61K 8/898* (2013.01); *A61Q 5/02* (2013.01); *A61K 2800/436* (2013.01); *A61K 2800/48* (2013.01); *A61K 2800/546* (2013.01); *A61K 2800/596* (2013.01)

(56) References Cited

U.S. PATENT DOCUMENTS

| | | | |
|---|---|---|---|
| 5,543,074 | A | 6/1996 | Hague |
| 5,977,039 | A | 2/1999 | Gordon et al. |
| 6,001,344 | A | 12/1999 | Villa |
| 6,063,857 | A | 5/2000 | Greenblatt et al. |
| 6,106,816 | A | 8/2000 | Hitchen |
| 6,906,016 | B1 | 6/2005 | Tsaur |
| 7,541,320 | B2 | 2/2009 | Dabkowski |
| 8,642,056 | B2 | 2/2014 | Souzy et al. |
| 2003/0108503 | A1 | 6/2003 | Maubru et al. |
| 2010/0009891 | A1 | 1/2010 | Canto et al. |
| 2014/0112966 | A1 | 4/2014 | Souzy et al. |
| 2014/0178325 | A1* | 6/2014 | Martinez-Castro .... C09D 5/024 424/70.16 |
| 2014/0336101 | A1* | 11/2014 | Mertens ................ C08F 220/18 510/476 |
| 2017/0027846 | A1 | 2/2017 | Souzy et al. |

FOREIGN PATENT DOCUMENTS

| | | |
|---|---|---|
| EP | 2853570 | 4/2015 |
| EP | 2933280 | 10/2015 |
| WO | WO9113145 | 9/1991 |
| WO | WO2012120330 | 9/2012 |
| WO | WO2016100466 | 6/2016 |
| WO | WO2017042004 | 3/2017 |
| WO | WO2017200786 | 11/2017 |

OTHER PUBLICATIONS

Search Report and Written Opinion in EP18155492; dated Jul. 4, 2018.
Search Report and Written Opinion in EP18155489.
Search Report and Written Opinion in EP18155490; dated Jul. 3, 2018; European Patent Office (EPO).
Search Report and Written Opinion in PCTEP2018078742; dated Nov. 22, 2018.
Search Report and Written Opinion in PCTEP2018078741.
Search Report and Written Opinion in PCTEP2018078743; dated Dec. 3, 2018.
Search Report and Written Opinion in PCTEP2018078740; dated Dec. 14, 2018.
Search Report and Written Opinion in EP19151019; dated May 17, 2019.
Robert Y Lochhead et al; A Review of Recent Advances in the Polymeric Delivery of Attributes in Cosmetics and Personal Care Products; Polymeric Delivery of Therpeatics; Jan. 1, 2010; 1-20 (also as XP055586489).
Search Report and Written Opinion in PCTEP2019086872; dated Feb. 27, 2020.

* cited by examiner

SHAMPOO COMPOSITION AND METHOD OF USE

CROSS REFERENCE TO RELATED APPLICATION

This application is a U.S. National Stage Application under 35 U.S.C. § 371 of International Application No. PCT/EP2018/078743, filed on Oct. 19, 2018, which claims the benefit of European Application No. 18155489.0, filed on Feb. 7, 2018 and U.S. Provisional Application No. 62/581,135 filed on Nov. 3, 2017, the entire disclosures of which are hereby incorporated by reference for any and all purposes.

FIELD OF THE INVENTION

The present invention relates to aqueous shampoo compositions, containing a silicone and a hydrophobically modified alkali swellable emulsion (HASE) polymer as anti-settling thickening polymer, for use in the treatment of hair. The invention further relates to a method of treating hair by means of such compositions.

BACKGROUND AND PRIOR ART

Shampoo compositions having beneficial ingredients suspended are desirable to the consumer seeking to deliver benefit to their hair. Shampoo formulations have suspended materials that typically impart, or contribute to, certain user benefits, including: visual product aesthetics, various active effects and encapsulation/release of separate phases during use.

To be acceptable to consumers, such aqueous compositions desirably exhibit both an appealing look and feel. Such suspensions, however, in complex aqueous formulations for rinse-off applications in home and personal care applications present significant challenges.

Notwithstanding, the benefits associated with the incorporation of cosmetic ingredients suspended in aqueous compositions, their incorporation creates a variety of complications. For example, cosmetic ingredients typically have a density disparate from the continuous phase of the composition. This density mismatch can lead to compositional instability. In systems containing insoluble materials with a density less than that of the continuous phase, the cosmetic ingredients tend to float to the top surface of the continuous phase (i.e., creaming). In systems containing insoluble materials with a density greater than that of the continuous phase, the insoluble materials tend to sink to the bottom of the continuous phase (i.e., settling).

To further exacerbate the complications associated with the desirable incorporation of cosmetic ingredients suspended in aqueous shampoo compositions, many of these compositions are desirably provided at acidic pH. As a result, conventional anti-settling, thickening polymers fail to provide adequate stability for such low pH compositions.

Commercial products have utilized cationic polymers as structurants. For instance, U.S. Pat. No. 7,541,320 (Unilever) discloses a cationically modified cellulose in a cleansing system that includes alkyl ether sulfate (3 EO), cocoamidopropylbetaine and cocoamidopropylhydroxysultaine, and as a conditioning active a non-volatile silicone. U.S. Pat. No. 4,298,494 (Lever Brothers) reports use of a cationic derivative of polygalactomannan gum to stabilize a sodium alkyl sulfate and alkyl ether sulfate surfactant system.

Another group of commercially popular structurants are the acrylic polymers, particularly those known as Carbomers. For example, U.S. Pat. No. 5,543,074 (Chesebrough-Ponds) and U.S. Pat. No. 5,977,039 (Helene Curtis) regulate silicone deposition through use of crosslinked polymers of acrylic acid, commercially available under the trademark Carbopol (R). U.S. Pat. No. 6,001,344 (Unilever) utilizes structurant combinations of xanthan gum and Carbopol (R) for stabilizing liquid cleansing compositions. U.S. Pat. No. 6,906,016 (Unilever) reports liquid cleansers structured with soluble and water swellable starches combined with linear Cs-Ci3 fatty acids. U.S. Patent Application Publication 2010/0009891 (Unilever) reports personal care liquid compositions formulated with a bacterially produced microfibrous cellulose as a suspending system.

An approach to the suspending of insoluble materials in an aqueous cleansing formulation is disclosed in U.S. Pat. No. 8,642,056 to Souzy, et al. Souzy, et al. disclose a method for thickening a formulation, comprising contacting a cosmetic formulation with a direct aqueous emulsion of a polymer, followed by regulation of the pH to a value between 5 and 7, thereby forming a thickened formulation, wherein the emulsion is free from surfactants and organic solvents other than water and the polymer consists, expressed as a % by weight of each of the monomers therein, of: a) 20% to 60% by weight of methacrylic acid and/or acrylic acid, where the % by weight of acrylic acid, if present, compared to the total weight of acrylic acid and methacrylic acid is at least 50%, b) 40% to 80% by weight of at least one monomer chosen from among ethyl acrylate, butyl acrylate, and methyl methacrylate, c) 0.5% to 25% by weight of a monomer comprising a hydrophobic group, d) 0.05% to 22% by weight of 2-acrylamido-2-methylpropane sulfonic acid, and e) 0 to 1% by weight of at least one cross-linked monomer, wherein the monomer comprising a hydrophobic group has the general formula:

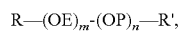

R—(OE)$_m$-(OP)$_n$—R', m and n are integers of less than or equal to 150, at least one of which is non-zero, OE and OP are respectively ethylene oxide and propylene oxide, R is a polymerizable group selected from the groups consisting of methacrylate and methacrylurethane groups, R' is a hydrophobic group having at least 6 and at most 36 carbon atoms.

Another approach to the suspending of insoluble materials in an aqueous cleansing formulation is disclosed in U.S. Pat. No. 6,106,816 to Hitchen. Hitchen discloses an aqueous conditioning shampoo composition comprising, in addition to water: (a) from 2 to 40% by weight of surfactant selected from the group consisting of anionic, nonionic and amphoteric surfactants, and mixtures thereof; (b) from 0.01 to 10% by weight of insoluble, non-volatile silicone which conditions hair; (c) from 0.01 to 3% by weight of titanium dioxide coated mica particles dispersed in the shampoo matrix; and (d) from 0.2 to 3% by weight of a crosslinked acrylic acid polymer for suspending the dispersed titanium dioxide coated mica particles and preventing them from settling in the composition as well as the insoluble, non-volatile silicone conditioning agent from creaming to the top of the composition on standing.

Additionally, in acidic pH aqueous compositions, conventional hydrophobically modified alkali swellable emulsions (HASE) polymers, used for anti-settling and thickening applications, can have the effect of reducing the deposition of the included cosmetic ingredients (for example; silicone oil droplets) to the hair and the scalp. Aqueous compositions comprising other available thickening polymers are able to deliver good deposition of cosmetic ingredients, but have compromised visual characteristics.

EP2933280 discloses aqueous shampoo compositions comprising HASE copolymers which comprise a) 10 to 80 percent by weight of methacrylic acid and, optionally, of acrylic acid; b)15 to 80 percent by weight of at least one non-ionic vinyl monomer; c) 0.05 to 9.5 percent by weight of 2-acrylamido-2-methylpropane sulfonic acid or a salt thereof; d) 0.5 to 30 percent by weight of at least one monomer containing at least one hydrophobic group; and e) 0.01 to 5 percent by weight of at least one crosslinking monomer. The copolymers are said to be useful for thickening personal care or cosmetic formulations in acidic conditions. Accordingly, there is a need for a composition that provides superior visual characteristics, without impairing other product attributes such as stability and benefit performance.

It is well known that the addition of thickening polymers causes a reduction in the transparency of a composition to which they are added. This can be demonstrated by starting with a highly transparent simple aqueous composition, comprising for example, surfactant and water, and then adding a thickening polymer. The resultant reduction in transparency of the composition can be clearly observed. However, we have now surprisingly found that the high visual transparency of the starting aqueous composition is preserved upon addition of the specific anti-settling thickening polymer, herein defined. The impact of this high transparency has a positive visual effect even after insoluble ingredients, such as mica, titanium dioxide or silicone are subsequently added to the composition. Whilst no longer transparent, the resulting composition has an improved visual appearance that is appealing for the consumer. We believe that the polymer for use in the compositions of the invention prevents aggregation of suspended material, which results in reduced turbidity and higher reflection of light from the surfaces of the suspended material, thus resulting in the improved visual appearance.

We have now found that an aqueous composition comprising a specific anti-settling thickening polymer, herein defined, provides superior visual properties, whilst maintaining good levels of deposition of a benefit agent as well as stability.

Definition of the Invention

A first aspect of the invention provides an acidic aqueous shampoo composition, which comprises:
(I) a cleansing surfactant selected from the group consisting of anionic surfactant, zwitterionic or amphoteric surfactant and nonionic surfactant;
(II) an emulsified silicone,
(III) an anti-settling, thickening polymer,
wherein the anti-settling, thickening polymer, comprises:
  (a) 40 to 74.5 wt % of structural units of $C_{1-4}$ alkyl acrylate;
  (b) 20 to 50 wt % of structural units of methacrylic acid;
  (c) 0.3 to <5 wt % of structural units of 2-acrylamido-2-methylpropane sulfonic acid (AMPS);
  (d) 5 to 25 wt % of structural units of a specialized associated monomer having the following structure:

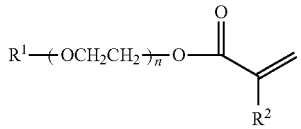

wherein $R^1$ is a linear saturated $C_{10-24}$ alkyl group; wherein $R^2$ is a hydrogen or a methyl group (preferably, wherein $R^2$ is a methyl group); and wherein n is an average of 20 to 28; with the proviso that the structural units of the specialized associated monomer (d) are derived from one of (i) a single specialized associated monomer (preferably, a single specialized associated monomer wherein $R^1$ is selected from the group consisting of a linear saturated $C_{12}$ alkyl group, a linear saturated $C_{18}$ alkyl group and a linear saturated $C_{22}$ alkyl group; more preferably, a single specialized associated monomer wherein $R^1$ is selected from the group consisting of a linear saturated $C_{12}$ alkyl group and a linear saturated $C_{18}$ alkyl group); (ii) two specialized associated monomers, wherein $R^1$ is, respectively, a linear saturated $C_{12}$ and a linear saturated $C_{18}$ alkyl group; or (iii) two specialized associated monomers, wherein $R^1$ is, respectively, a linear saturated $C_{18}$ alkyl group and a linear saturated $C_{22}$ alkyl group;

(e) 0 to 1 wt % of structural units of acrylic acid; and
  (f) 0 to 2 wt % of structural units of multi-ethylenically unsaturated crosslinking monomer or chain transfer agent; and
wherein the sum of the weight percentages of structural units (a)-(f) is equal to 100 wt % of the anti-settling, thickening polymer.

A second aspect of the invention provides a method of treating a surface comprising the step of applying to the surface a composition of the first aspect of the invention.

In the method of the invention, the preferred surface is hair.

The method of the invention preferably further comprises the additional step of rinsing the surface with water.

General Description of the Invention

The aqueous shampoo composition of the present invention contains an anti-settling thickening polymer, for use in the treatment of surfaces.

The Anti-Settling Thickening Polymer

The anti-settling, thickening polymer for use in the aqueous compositions of the invention, comprises: (a) 40 to 74.5 wt % (preferably, 45 to 69.5 wt %; more preferably, 50 to 65 wt %; most preferably, 52 to 60 wt %) of structural units of $C_{1-4}$ alkyl acrylate (preferably, $C_{2-4}$ alkyl acrylate; more preferably, $C_{2-3}$ alkyl acrylate; most preferably, ethyl acrylate); (b) 20 to 50 wt % (preferably, 25 to 45 wt %; more preferably, 25 to 40 wt %; most preferably, 30 to 35 wt %) of structural units of methacrylic acid; (c) 0.3 to <5 wt % (preferably, 0.5 to 3 wt %; more preferably, 0.5 to 1.5 wt %; most preferably, 0.5 to 1.0 wt %) of structural units of 2-acrylamido-2-methylpropane sulfonic acid (AMPS); (d) 5 to 25 wt % (preferably, 7.5 to 22.5 wt %; more preferably, 10 to 20 wt %; most preferably, 12.5 to 18 wt %) of structural units of a specialized associated monomer having the following structure (formula 1):—

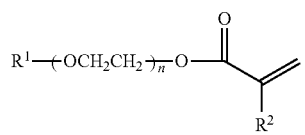

wherein $R^1$ is a linear saturated $C_{10-24}$ alkyl group; wherein $R^2$ is a hydrogen or a methyl group (preferably, wherein $R^2$ is a methyl group); and wherein n is an average of 20 to 28; with the proviso that the structural units of the specialized associated monomer (d) are derived from one of (i) a single specialized associated monomer (preferably, a single specialized associated monomer wherein $R^1$ is selected from the group consisting of a linear saturated $C_{12}$ alkyl group, a linear saturated $C_{18}$ alkyl group and a linear saturated $C_{22}$ alkyl group; more preferably, a single specialized associated monomer wherein $R^1$ is selected from the group consisting of a linear saturated $C_{12}$ alkyl group and a linear saturated $C_{18}$ alkyl group); (ii) two specialized associated monomers, wherein $R^1$ is, respectively, a linear saturated $C_{12}$ and a linear saturated $C_{18}$ alkyl group; or (iii) two specialized associated monomers, wherein $R^1$ is, respectively, a linear saturated $C_{18}$ alkyl group and a linear saturated $C_{22}$ alkyl group; (e) 0 to 1 wt % (preferably, 0 to 0.1 wt %; more preferably, 0 to 0.01 wt %; most preferably, 0) of structural units of acrylic acid; and (f) 0 to 2 wt % (preferably, 0 to 0.1 wt %; more preferably, 0 to 0.001 wt %; most preferably, 0 wt %) of structural units of multi-ethylenically unsaturated crosslinking monomer and chain transfer agent; wherein the sum of the weight percentages of structural units (a)-(f) is equal to 100 wt % of the anti-settling, thickening polymer.

Preferably, the anti-settling, thickening polymer for use in the aqueous compositions of the invention, comprises: (a) 50 to 65 wt % of structural units of ethyl acrylate; (b) 25 to 40 wt % of structural units of methacrylic acid; (c) 0.5 to 1.5 wt % of structural units of 2-acrylamido-2-methylpropane sulfonic acid (AMPS); (d) 10 to 20 wt % of structural units of the specialized associated monomer; (e) 0 to 0.1 wt % of structural units of acrylic acid; and (f) 0 to 0.1 wt % (preferably, 0 to 0.001 wt %; more preferably, 0 wt %) of structural units of multi-ethylenically unsaturated crosslinking monomer and chain transfer agent; wherein the sum of the weight percentages of structural units (a)-(f) is equal to 100 wt % anti-settling, thickening polymer.

Preferably, the anti-settling, thickening polymer for use in the aqueous compositions of the invention has a weight average molecular weight of 5,000,000 to 400,000,000 Daltons. More preferably, the anti-settling, thickening polymer for use in the aqueous compositions of the invention has a weight average molecular weight of 25,000,000 to 300,000,000 Daltons. Most preferably, the anti-settling, thickening polymer for use in the aqueous compositions of the invention has a weight average molecular weight of 175,000,000 to 275,000,000 Daltons.

In reference to the anti-settling thickening polymer the weight average molecular weight refers to the weight average molecular weight as measured using asymmetric flow field flow fractionation (AF4) with inline Multi-Angle Light Scattering (MALS) and differential Refractive Index (RI) detections. The AF4 instrument used consisted of an Eclipse™ DualTec™ separation system (from Wyatt Technology Corp.) that was coupled in series to an 18 angle multi-angle light scattering (MALS) detector (DAWN HELOS II; from Wyatt Technology Corp.) and a differential refractometer (RI) (Optilab rEX; from Wyatt Technology Corp.). Flows through the AF4 instrument were provided using an Agilent Technologies 1200 series isocratic pump equipped with a micro-vacuum degasser. All injections were performed with an auto sampler (Agilent Technologies 1200 series). Data from the AF4 instrument were collected and processed using Astra software version 7.0.1.23 (from Wyatt Technology Corp.). Samples were prepared at a concentration of 1 mg/mL in 20 mM ammonium acetate solution at pH 10 (filtered with a 1.2 μm pore nylon membrane). Samples (25 μL) were injected into the standard separation channel system (25 cm long and a width dimension starting at 2.15 cm and reducing to 0.3 cm over the length) with a channel thickness of 350 μm and equipped with a 10 kDA cutoff regenerated cellulose ultrafiltration membrane (Wyatt Technology). The mobile phase used for the AF4 analysis was 20 mM ammonium acetate solution at pH 10. Separation was performed with an applied channel flow of 1 mL/min. The sample was introduced to the channel with a focus flow at 1.7 mL/min for 3 minutes. The elution flow as then started at 0.5 mL/min for 3 minutes and then followed by a linearly decreasing cross flow gradient (from 0.5 mL/min to 0.05 mL/min over 12 minutes), then a hold at 0.05 mL/min for another 5 minutes. The average molecular weight was calculated using Astra software version 7.0.1.23 after subtracting a blank injection with a refractive index increment (dn/dc) of 0.190 mL/g for all calculation with Berry model $2^{nd}$ order fit. Molecular weights are reported herein in units of Daltons.

Preferably, the structural units of $C_{1-4}$ alkyl acrylate in the anti-settling, thickening polymer for use in the aqueous compositions of the invention are structural units of $C_{2-4}$ alkyl acrylate. More preferably, the structural units of $C_{1-4}$ alkyl acrylate in the anti-settling, thickening polymer for use in the aqueous compositions of the invention are structural units of $C_{2-3}$ alkyl acrylate. Most preferably, the structural units of $C_{1-4}$ alkyl acrylate in the anti-settling, thickening polymer for use in the aqueous compositions of the invention are structural units of ethyl acrylate.

Preferably, the anti-settling, thickening polymer for use in the aqueous compositions of the invention comprises 40 to 74.5 wt % of structural units of $C_{1-4}$ alkyl acrylate (preferably, $C_{2-4}$ alkyl acrylate; more preferably, $C_{2-3}$ alkyl acrylate; most preferably, ethyl acrylate). More preferably, the anti-settling, thickening polymer for use in the aqueous compositions of the invention comprises 45 to 69.5 wt % of structural units of $C_{1-4}$ alkyl acrylate (preferably, $C_{2-4}$ alkyl acrylate; more preferably, $C_{2-3}$ alkyl acrylate; most preferably, ethyl acrylate). Still more preferably, the anti-settling, thickening polymer for use in the aqueous compositions of the invention comprises 50 to 65 wt % of structural units of $C_{1-4}$ alkyl acrylate (preferably, $C_{2-4}$ alkyl acrylate; more preferably, $C_{2-3}$ alkyl acrylate; most preferably, ethyl acrylate). Most preferably, the anti-settling, thickening polymer for use in the aqueous compositions of the invention comprises 52 to 60 wt % of structural units of $C_{1-4}$ alkyl acrylate (preferably, $C_{2-4}$ alkyl acrylate; more preferably, $C_{2-3}$ alkyl acrylate; most preferably, ethyl acrylate).

Preferably, the anti-settling, thickening polymer for use in the aqueous compositions of the invention comprises 20 to 50 wt % of structural units of methacrylic acid. More preferably, the anti-settling, thickening polymer for use in the aqueous compositions of the invention comprises 25 to 45 wt % of structural units of methacrylic acid. Still more preferably, the anti-settling, thickening polymer for use in the aqueous compositions of the invention comprises 25 to 40 wt % of structural units of methacrylic acid. Most preferably, the anti-settling, thickening polymer for use in the aqueous compositions of the invention comprises 30 to 35 wt % of structural units of methacrylic acid.

Preferably, the anti-settling, thickening polymer for use in the aqueous compositions of the invention comprises 0.3 to <5 wt % of structural units of 2-acrylamido-2-methylpropane sulfonic acid (AMPS), for example 0.3 to 4.5 wt %. More preferably, the anti-settling, thickening polymer for use in the aqueous compositions of the invention comprises 0.5 to 3 wt % of structural units of 2-acrylamido-2-methylpropane sulfonic acid (AMPS). Even more preferably, the anti-settling, thickening polymer for use in the aqueous compositions of the invention comprises 0.5 to 1.5 wt % of structural units of 2-acrylamido-2-methylpropane sulfonic acid (AMPS). Most preferably, the anti-settling, thickening polymer for use in the aqueous compositions of the invention comprises 0.5 to 1.0, of structural units of 2-acrylamido-2-methylpropane sulfonic acid (AMPS).

Preferably, the anti-settling, thickening polymer for use in the aqueous compositions of the invention comprises 5 to 25 wt % of structural units of a specialized associated monomer having the following structure:

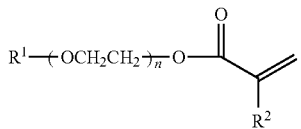

wherein $R^1$ is a linear saturated $C_{10\text{-}24}$ alkyl group; wherein $R^2$ is a hydrogen or a methyl group (preferably, wherein $R^2$ is a methyl group); and wherein n is an average of 20 to 28; with the proviso that the structural units of the specialized associated monomer (d) are derived from one of (i) a single specialized associated monomer (preferably, a single specialized associated monomer wherein $R^1$ is selected from the group consisting of a linear saturated $C_{12}$ alkyl group, a linear saturated $C_{18}$ alkyl group and a linear saturated $C_{22}$ alkyl group; more preferably, a single specialized associated monomer wherein $R^1$ is selected from the group consisting of a linear saturated $C_{12}$ alkyl group and a linear saturated $C_{18}$ alkyl group); (ii) two specialized associated monomers, wherein $R^1$ is, respectively, a linear saturated $C_{12}$ and a linear saturated $C_{18}$ alkyl group; or (iii) two specialized associated monomers, wherein $R^1$ is, respectively, a linear saturated $C_{18}$ alkyl group and a linear saturated $C_{22}$ alkyl group. More preferably, the anti-settling, thickening polymer for use in the aqueous compositions of the invention comprises 7.5 to 22.5 wt % of structural units of a specialized associated monomer having the following structure:

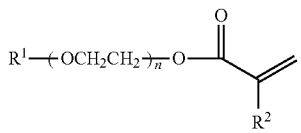

wherein $R^1$ is a linear saturated $C_{10\text{-}24}$ alkyl group; wherein $R^2$ is a hydrogen or a methyl group (preferably, wherein $R^2$ is a methyl group); and wherein n is an average of 20 to 28; with the proviso that the structural units of the specialized associated monomer (d) are derived from one of (i) a single specialized associated monomer (preferably, a single specialized associated monomer wherein $R^1$ is selected from the group consisting of a linear saturated $C_{12}$ alkyl group, a linear saturated $C_{18}$ alkyl group and a linear saturated $C_{22}$ alkyl group; more preferably, a single specialized associated monomer wherein $R^1$ is selected from the group consisting of a linear saturated $C_{12}$ alkyl group and a linear saturated $C_{18}$ alkyl group); (ii) two specialized associated monomers, wherein $R^1$ is, respectively, a linear saturated $C_{12}$ and a linear saturated $C_{18}$ alkyl group; or (iii) two specialized associated monomers, wherein $R^1$ is, respectively, a linear saturated $C_{18}$ alkyl group and a linear saturated $C_{22}$ alkyl group. Still more preferably, the anti-settling, thickening polymer for use in the aqueous compositions of the invention comprises 10 to 20 wt % of structural units of a specialized associated monomer having the following structure:

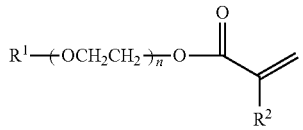

wherein $R^1$ is a linear saturated $C_{10\text{-}24}$ alkyl group; wherein $R^2$ is a hydrogen or a methyl group (preferably, wherein $R^2$ is a methyl group); and wherein n is an average of 20 to 28; with the proviso that the structural units of the specialized associated monomer (d) are derived from one of (i) a single specialized associated monomer (preferably, a single specialized associated monomer wherein $R^1$ is selected from the group consisting of a linear saturated $C_{12}$ alkyl group, a linear saturated $C_{18}$ alkyl group and a linear saturated $C_{22}$ alkyl group; more preferably, a single specialized associated monomer wherein $R^1$ is selected from the group consisting of a linear saturated $C_{12}$ alkyl group and a linear saturated $C_{18}$ alkyl group); (ii) two specialized associated monomers, wherein $R^1$ is, respectively, a linear saturated $C_{12}$ and a linear saturated $C_{18}$ alkyl group; or (iii) two specialized associated monomers, wherein $R^1$ is, respectively, a linear saturated $C_{18}$ alkyl group and a linear saturated $C_{22}$ alkyl group. Most preferably, the anti-settling, thickening polymer for use in the aqueous compositions of the invention comprises 12.5 to 18 wt % of structural units of a specialized associated monomer having the following structure:

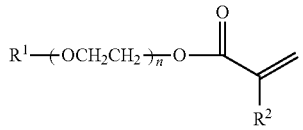

wherein $R^1$ is a linear saturated $C_{10\text{-}24}$ alkyl group; wherein $R^2$ is a hydrogen or a methyl group (preferably, wherein $R^2$ is a methyl group); and wherein n is an average of 20 to 28; with the proviso that the structural units of the specialized associated monomer (d) are derived from one of (i) a single specialized associated monomer (preferably, a single specialized associated monomer wherein $R^1$ is selected from the group consisting of a linear saturated $C_{12}$ alkyl group, a linear saturated $C_{18}$ alkyl group and a linear saturated $C_{22}$ alkyl group; more preferably, a single specialized associated monomer wherein $R^1$ is selected from the group consisting of a linear saturated $C_{12}$ alkyl group and a linear saturated $C_{18}$ alkyl group); (ii) two specialized associated monomers, wherein $R^1$ is, respectively, a linear saturated $C_{12}$ and a linear saturated $C_{18}$ alkyl group; or (iii) two specialized associated monomers, wherein $R^1$ is, respectively, a linear saturated $C_{18}$ alkyl group and a linear saturated $C_{22}$ alkyl group.

Preferably, the anti-settling, thickening polymer for use in the aqueous compositions of the invention includes 0 to 1 wt % of structural units of acrylic acid. More preferably, the anti-settling, thickening polymer for use in the aqueous compositions of the invention includes 0 to 0.1 wt % of structural units of acrylic acid. Still more preferably, anti-settling, thickening polymer for use in the aqueous compositions of the invention contains 0 to 0.01 wt % of structural units of acrylic acid. Yet still more preferably, the anti-settling, thickening polymer for use in the aqueous compositions of the invention includes less than the detectable limit of structural units of acrylic acid. Most preferably, the anti-settling, thickening polymer for use in the aqueous compositions of the invention contains 0 wt % structural units of acrylic acid.

Preferably, the anti-settling, thickening polymer for use in the aqueous compositions of the invention comprises 0 to 2 wt % of structural units of multi-ethylenically unsaturated crosslinking monomer and chain transfer agent. More preferably, the anti-settling, thickening polymer for use in the aqueous compositions of the invention comprises 0 to 0.1 wt % of structural units of multi-ethylenically unsaturated crosslinking monomer and chain transfer agent. Still more preferably, the anti-settling, thickening polymer for use in the aqueous compositions of the invention comprises 0 to 0.001 wt % of structural units of multi-ethylenically unsaturated crosslinking monomer and chain transfer agent. Yet still more preferably, the anti-settling, thickening polymer for use in the aqueous compositions of the invention includes less than the detectable limit of structural units of multi-ethylenically unsaturated crosslinking monomer and chain transfer agent. Most preferably, the anti-settling, thickening polymer for use in the aqueous compositions of the invention contains 0 wt % structural units of multi-ethylenically unsaturated crosslinking monomer and chain transfer agent.

Preferably, the anti-settling, thickening polymer for use in the aqueous compositions of the invention includes less than 0.001 wt % of structural units of multi-ethylenically unsaturated crosslinking monomer. More preferably, the anti-settling, thickening polymer for use in the aqueous compositions of the invention includes less than 0.0001 wt % of structural units of multi-ethylenically unsaturated crosslinking monomer. Still more preferably, anti-settling, thickening polymer for use in the aqueous compositions of the invention contains less than the detectable limit of structural units of multi-ethylenically unsaturated crosslinking monomer. Most preferably, the anti-settling, thickening polymer for use in the aqueous compositions of the invention includes 0 wt % of structural units of multi-ethylenically unsaturated crosslinking monomer.

Preferably, the anti-settling, thickening polymer for use in the aqueous compositions of the invention includes less than 0.1 wt % of structural units of chain transfer agent. More preferably, the anti-settling, thickening polymer for use in the aqueous compositions of the invention includes less than 0.001 wt % of structural units of chain transfer agent. Still more preferably, anti-settling, thickening polymer for use in the aqueous compositions of the invention contains less than the detectable limit of structural units of chain transfer agent. Most preferably, the anti-settling, thickening polymer for use in the aqueous compositions of the invention includes 0 wt % of structural units of chain transfer agent.

Preferably, the anti-settling, thickening polymer for use in the aqueous compositions of the invention includes less than 0.001 wt % of structural units of multi-ethylenically unsaturated crosslinking monomer and less than 0.1 wt % of structural units of chain transfer agent. More preferably, the anti-settling, thickening polymer for use in the aqueous compositions of the invention includes less than 0.0001 wt % of structural units of multi-ethylenically unsaturated crosslinking monomer and less than 0.01 wt % of structural units of chain transfer agent. Still more preferably, anti-settling, thickening polymer for use in the aqueous compositions of the invention contains less than the detectable limit of structural units of multi-ethylenically unsaturated crosslinking monomer and less than the detectable limit of structural units of chain transfer agent. Most preferably, the anti-settling, thickening polymer for use in the aqueous compositions of the invention includes 0 wt % of structural units of multi-ethylenically unsaturated crosslinking monomer and includes 0 wt % of structural units of chain transfer agents.

One of ordinary skill in the art will know to select appropriate multi-ethylenically unsaturated crosslinking monomers to provide any structural units of multi-ethylenically unsaturated crosslinking monomer in the anti-settling, thickening polymer for use in the aqueous compositions of the invention. Structural units of multi-ethylenically unsaturated crosslinking monomer may include for example those derived from polyunsaturated monomer components including, polyunsaturated aromatic monomers (e.g., divinyl benzene, divinyl naphthalene, trivinyl benzene); polyunsaturated alicyclic monomers (e.g., 1,2,4-trivinylcyclohexane); difunctional esters of phthalic acid (e.g., diallyl phthalate); polyunsaturated aliphatic monomers (e.g., isoprene, butadiene, 1,5-hexadiene, 1,5,9-decatriene, 1,9-decadiene, 1,5-heptadiene); polyalkenyl ethers (e.g., trially pentaerythritol, diallyl pentaerythritol, diallyl sucrose, octaally sucrose, trimethylolpropane diallyl ether); polyunsaturated esters of polyalcohols or polyacids (e.g., 1,6-hexanediol di(meth)acrylate, tetramethylene tri(meth)acrylate, allyl acrylate, diallyl itaconate, diallyl fumarate, diallyl maleate, trimethylolpropane tri(meth)acrylate, trimethylolpropane di(meth)acrylate, polyethylene glycol di(meth)acrylate); alkylene bisacrylamides (e.g., methylene bisacrylamide, propylene bisacrylamide); hydroxy and carboxy derivatives of methylene bis-acrylamide (e.g., N,N'-bismethylol methylene bisacrylamide); polyethyleneglycol di(meth)acrylates (e.g., ethyleneglycol di(meth)acrylate, diethyleneglycol di(meth)acrylate, triethyleneglycol di(meth)acrylate); polyunsaturated silanes (e.g., dimethyldivinylsilane, methyltrivinylsilane, allyldimethylvinylsilane, diallyldimethylsilane, tetravinylsilane); polyunsaturated stannanes (e.g., tetraallyl tin, diallyldimethyl tin) and the like.

One of ordinary skill in the art will know to select appropriate chain transfer agents to provide any structural units of chain transfer agents in the anti-settling, thickening polymer for use in the aqueous compositions of the invention. Structural units of chain transfer agents may monomer include those derived from a variety of thio and disulfide containing compounds (e.g., $C_{1-18}$ alkyl mercaptans, mercaptocarboxylic acids, mercaptocarboxylic esters, thioesters, $C_{1-18}$ alkyl disulfides, aryldisulfides, polyfunctional thiols); phosphites and hypophosphites; haloalkyl compounds (e.g., carbon tetrachloride, bromotrichloromethane) and unsaturated chain transfer agents (e.g., alpha-methylstyrene).

Preferably, the shampoo of the present invention, includes from 0.05 to 4 wt % of the anti-settling, thickening polymer more preferably from 0.05 to 3 wt %, still more preferably from 0.1 to 1 wt % and most preferably from 0.2 to 0.8 wt % by weight of total composition.

The Cleansing Surfactant

The composition of the present invention comprises a surfactant selected from the group consisting of anionic surfactants, nonionic surfactants, zwitterionic surfactants and mixtures thereof.

Preferably, the cleansing surfactant is selected from the group consisting of sodium lauryl sulphate, sodium lauryl ether sulphate (n)EO, (where n is from 1 to 3, preferably 2 to 3, most preferably 3), ammonium lauryl sulphate, ammonium lauryl ether sulphate(n)EO, (where n is from 1 to 3, preferably 2 to 3, most preferably 3), sodium cocoyl isethionate and lauryl ether carboxylic acid, coco betaine, cocamidopropyl betaine, sodium cocoamphoacetate and mixtures thereof.

Preferably, mixtures of any of the anionic, non-ionic and amphoteric cleansing surfactants has a ratio of primary to secondary surfactant of between 1:1-10:1, more preferably 2:1-9:1 and most preferably 3:1-8:1, based on the inclusion weight of the cleansing surfactant in the shampoo composition.

Preferably, the composition of the present invention comprises from 1 to 50%, preferably from 2 to 40%, more preferably from 4 to 25% of total surfactant, based on the total weight of the composition.

The Silicone

The compositions of the invention comprise, emulsified droplets of a silicone conditioning agent, for enhancing conditioning performance.

The emulsified silicone is preferably selected from the group consisting of polydiorganosiloxanes, silicone gums, amino functional silicones and mixtures thereof.

Suitable silicones include polydiorganosiloxanes, in particular polydimethylsiloxanes which have the CTFA designation dimethicone. Also suitable for use compositions of the invention (particularly shampoos and conditioners) are polydimethyl siloxanes having hydroxyl end groups, which have the CTFA designation dimethiconol. Also suitable for use in compositions of the invention are silicone gums having a slight degree of cross-linking, as are described for example in WO 96/31188.

The viscosity of the emulsified silicone itself (not the emulsion or the final hair conditioning composition) is typically at least 10,000 cst at 25° C. the viscosity of the silicone itself is preferably at least 60,000 cst, most preferably at least 500,000 cst, ideally at least 1,000,000 cst. Preferably the viscosity does not exceed $10^9$ cst for ease of formulation.

Emulsified silicones for use in the shampoo compositions of the invention will typically have a D90 silicone droplet size in the composition of less than 30, preferably less than 20, more preferably less than 10 micron, ideally from 0.01 to 1 micron. Silicone emulsions having an average silicone droplet size (D50) of 0.15 micron are generally termed microemulsions.

Silicone particle size may be measured by means of a laser light scattering technique, for example using a 2600D Particle Sizer from Malvern Instruments.

Examples of suitable pre-formed emulsions include Xiameter MEM 1785 and microemulsion DC2-1865 available from Dow Corning. These are emulsions/microemulsions of dimethiconol. Cross-linked silicone gums are also available in a pre-emulsified form, which is advantageous for ease of formulation.

A further preferred class of silicones for inclusion in shampoos and conditioners of the invention are amino functional silicones. By "amino functional silicone" is meant a silicone containing at least one primary, secondary or tertiary amine group, or a quaternary ammonium group. Examples of suitable amino functional silicones include: polysiloxanes having the CTFA designation "amodimethicone".

Specific examples of amino functional silicones suitable for use in the invention are the aminosilicone oils DC2-8220, DC2-8166 and DC2-8566 (all ex Dow Corning).

Suitable quaternary silicone polymers are described in EP-A-0 530 974. A preferred quaternary silicone polymer is K3474, ex Goldschmidt.

Also suitable are emulsions of amino functional silicone oils with non ionic and/or cationic surfactant.

Pre-formed emulsions of amino functional silicone are also available from suppliers of silicone oils such as Dow Corning and General Electric. Specific examples include DC939 Cationic Emulsion and the non-ionic emulsions DC2-7224, DC2-8467, DC2-8177 and DC2-8154 (all ex Dow Corning).

The total amount of silicone is preferably from 0.01 wt % to 10% wt of the total composition more preferably from 0.1 wt % to 5 wt %, most preferably 0.5 wt % to 3 wt % is a suitable level.

In a preferred embodiment, the aqueous composition of the invention comprises at least one insoluble conditioning agent and at least one other cosmetic ingredient. Preferably, the at least one oily conditioning agent is selected from a silicone and a non-silicone oily conditioning agent.

Cosmetic ingredients are preferably selected from the group consisting of at least one of an antibacterial agent, a foam booster, a perfume, encapsulates (for example encapsulated fragrance) a dye, a colouring agent, a pigment, a preservative, a thickener, a protein, a phosphate ester, a buffering agent, a pH adjusting agent, an opacifier, a viscosity modifier, an emollient, a sunscreen, an emulsifier, a sensate active (for example menthol and menthol derivatives), vitamins, mineral oils, essential oils, lipids, natural actives, glycerine, natural hair nutrients such as botanicals, fruit extracts, sugar derivatives and amino acids, microcrystalline cellulose and mixtures thereof.

Preferably, the aqueous composition of the present invention includes from 0.01 to 20 wt % of the cosmetic ingredient, more preferably from 0.05 to 10 wt %, still more preferably from 0.075 to 7.5 wt % and most preferably, from 0.1 to 5 wt % of the at least one cosmetic ingredient, by weight of the total composition.

pH of Compositions

The aqueous composition of the present invention preferably has a pH from 3 to <7 (for example 3 to 6.5), preferably 4 to <7, more preferably 4 to 6.5, most preferably from 4.2 to 6.5.

Pearlescer

The compositions of the present invention preferably include a pearlescer to improve visual appearance and/or consumer appeal of the product. Most preferably the pearlescer is selected from mica, titanium dioxide, titanium dioxide coated mica, ethylene glycol distearate (INCI glycol distearate) and mixtures thereof.

Shampoos

Shampoo compositions of the invention are generally aqueous, i.e. they have water or an aqueous solution or a lyotropic liquid crystalline phase as their major component.

Suitably, the shampoo composition will comprise from 50 to 98%, preferably from 60 to 92% water by weight based on the total weight of the composition.

Surfactants are compounds which have hydrophilic and hydrophobic portions that act to reduce the surface tension of the aqueous solutions they are dissolved in. Shampoo compositions according to the invention will generally comprise one or more cleansing surfactants, which are cosmetically acceptable and suitable for topical application to the hair. The cleansing surfactant may be chosen from anionic, non-ionic, amphoteric and zwitterionic compounds and mixtures thereof.

The total amount of cleansing surfactant in a shampoo composition for use in the invention is generally from 1 to 50%, preferably from 2 to 40%, more preferably from 4 to 25% by total weight surfactant based on the total weight of the composition.

Non-limiting examples cleansing surfactants include anionic cleansing surfactants include; alkyl sulphates, alkyl ether sulphates, alkaryl sulphonates, N-alkyl sarcosinates, alkyl phosphates, alkyl ether phosphates, acyl amino acid based surfactants, alkyl ether carboxylic acids, acyl taurates, acyl glutamates, alkyl glycinates and salts thereof, especially their sodium, magnesium, ammonium and mono-, di- and triethanolamine salts. The alkyl and acyl groups in the preceding list generally contain from 8 to 18, preferably from 10 to 16 carbon atoms and may be unsaturated. The alkyl ether sulphates, alkyl ether phosphates and alkyl ether carboxylic acids and salts thereof may contain from 1 to 20 ethylene oxide or propylene oxide units per molecule.

Further non-limiting examples of cleansing surfactants may include non-ionic cleansing surfactants including; aliphatic ($C_8$-$C_{18}$) primary or secondary linear or branched chain alcohols with alkylene oxides, usually ethylene oxide and generally having from 6 to 30 ethylene oxide groups. Other representative cleansing surfactants include mono- or di-alkyl alkanolamides (examples include coco mono-ethanolamide and coco mono-isopropanolamide) and alkyl polyglycosides (APGs). Suitable alkyl polyglycosides for use in the invention are commercially available and include for example those materials identified as: Plantapon 1200 and Plantapon 2000 ex BASF. Other sugar-derived surfactants, which can be included in compositions for use in the invention include the $C_{10}$-$C_{18}$ N-alkyl ($C_1$-$C_6$) polyhydroxy fatty acid amides, such as the $C_{12}$-$C_{18}$ N-methyl glucamides, as described for example in WO 92 06154 and U.S. Pat. No. 5,194,639, and the N-alkoxy polyhydroxy fatty acid amides, such as $C_{10}$-$C_{18}$ N-(3-methoxypropyl) glucamide.

Additional non-limiting examples of cleansing surfactants may include amphoteric or zwitterionic cleansing surfactants including; alkyl amine oxides, alkyl betaines, alkyl amidopropyl betaines, alkyl sulphobetaines (sultaines), alkyl glycinates, alkyl carboxyglycinates, alkyl amphoacetates, alkyl amphopropionates, alkylamphoglycinates, alkyl amidopropyl hydroxysultaines, acyl taurates and acyl glutamates, wherein the alkyl and acyl groups have from 8 to 19 carbon atoms.

Typical cleansing surfactants for use in shampoo compositions for use in the invention include sodium oleyl succinate, ammonium lauryl sulphosuccinate, sodium lauryl sulphate, sodium lauryl ether sulphate, sodium lauryl ether sulphosuccinate, ammonium lauryl sulphate, ammonium lauryl ether sulphate, sodium cocoyl isethionate, sodium lauryl isethionate, lauryl ether carboxylic acid and sodium N-lauryl sarcosinate, sodium pareth sulphate, cocodimethyl sulphopropyl betaine, lauryl betaine, coco betaine, cocamidopropyl betaine, sodium cocoamphoacetate.

Preferred cleansing surfactants are sodium lauryl sulphate, sodium lauryl ether sulphate (n)EO, (where n is from 1 to 3, preferably 2 to 3, most preferably 3), ammonium lauryl sulphate, ammonium lauryl ether sulphate(n)EO, (where n is from 1 to 3, preferably 2 to 3, most preferably 3), sodium cocoyl isethionate and lauryl ether carboxylic acid, coco betaine, cocamidopropyl betaine, sodium cocoamphoacetate.

Mixtures of any of the foregoing anionic, non-ionic and amphoteric cleansing surfactants may also be suitable, preferably where the primary to secondary surfactant ratio is between 1:1-10:1, more preferably 2:1-9:1 and most preferably 3:1-8:1, based on the inclusion weight of the cleansing surfactant in the shampoo composition.

Optionally, a shampoo composition for use in the invention may contain further ingredients, (non-limiting examples of which are described below) to enhance performance and/or consumer acceptability.

Cationic polymers are preferred ingredients in a shampoo composition for use in the invention for enhancing conditioning performance.

Suitable cationic polymers may be homopolymers which are cationically substituted or may be formed from two or more types of monomers. The weight average (Mw) molecular weight of the polymers will generally be between 100 000 and 3 million daltons. The polymers will have cationic nitrogen containing groups such as quaternary ammonium or protonated amino groups, or a mixture thereof. If the molecular weight of the polymer is too low, then the conditioning effect is poor. If too high, then there may be problems of high extensional viscosity leading to stringiness of the composition when it is poured.

The cationic nitrogen-containing group will generally be present as a substituent on a fraction of the total monomer units of the cationic polymer. Thus when the polymer is not a homopolymer it can contain spacer non-cationic monomer units. Such polymers are described in the CTFA Cosmetic Ingredient Directory, 3rd edition. The ratio of the cationic to non-cationic monomer units is selected to give polymers having a cationic charge density in the required range, which is generally from 0.2 to 3.0 meq/gm. The cationic charge density of the polymer is suitably determined via the Kjeldahl method as described in the US Pharmacopoeia under chemical tests for nitrogen determination.

Suitable cationic polymers include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have C1-C7 alkyl groups, more preferably C1-3 alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition. In general, secondary and tertiary amines, especially tertiary, are preferred.

Amine substituted vinyl monomers and amines can be polymerised in the amine form and then converted to ammonium by quaternization.

The cationic polymers can comprise mixtures of monomer units derived from amine- and/or quaternary ammonium-substituted monomer and/or compatible spacer monomers.

Suitable (non-limiting examples of) cationic polymers include:

cationic diallyl quaternary ammonium-containing polymers including, for example, dimethyldiallylammonium chloride homopolymer and copolymers of acrylamide and dimethyldiallylammonium chloride, referred to in the industry (CTFA) as Polyquaternium 6 and Polyquaternium 7, respectively;

mineral acid salts of amino-alkyl esters of homo- and co-polymers of unsaturated carboxylic acids having from 3 to 5 carbon atoms, (as described in U.S. Pat. No. 4,009,256);

cationic polyacrylamides (as described in WO95/22311).

Other cationic polymers that can be used include cationic polysaccharide polymers, such as cationic cellulose derivatives, cationic starch derivatives, and cationic guar gum derivatives. Cationic polysaccharide polymers suitable for use in compositions for use in the invention include monomers of the formula:

$$A-O-[R-N^+(R^1)(R^2)(R^3)X^-],$$

wherein: A is an anhydroglucose residual group, such as a starch or cellulose anhydroglucose residual. R is an alkylene, oxyalkylene, polyoxyalkylene, or hydroxyalkylene group, or combination thereof. $R^1$, $R^2$ and $R^3$ independently represent alkyl, aryl, alkylaryl, arylalkyl, alkoxyalkyl, or alkoxyaryl groups, each group containing up to about 18 carbon atoms. The total number of carbon atoms for each cationic moiety (i.e., the sum of carbon atoms in $R^1$, $R^2$ and $R^3$) is preferably about 20 or less, and X is an anionic counterion.

Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from the Amerchol Corporation, for instance under the tradename Polymer LM-200.

Other suitable cationic polysaccharide polymers include quaternary nitrogen-containing cellulose ethers (e.g. as described in U.S. Pat. No. 3,962,418), and copolymers of etherified cellulose and starch (e.g. as described in U.S. Pat. No. 3,958,581). Examples of such materials include the polymer LR and JR series from Dow, generally referred to in the industry (CTFA) as Polyquaternium 10.

A particularly suitable type of cationic polysaccharide polymer that can be used is a cationic guar gum derivative, such as guar hydroxypropyltrimethylammonium chloride (commercially available from Rhodia in their JAGUAR trademark series). Examples of such materials are JAGUAR C13S, JAGUAR C14 and JAGUAR C17.

Mixtures of any of the above cationic polymers may be used.

Cationic polymer will generally be present in a shampoo composition for use in the invention at levels of from 0.01 to 5%, preferably from 0.02 to 1%, more preferably from 0.05 to 0.8% by total weight of cationic polymer based on the total weight of the composition.

Unless otherwise indicated, ratios, percentages, parts, and the like, referred to herein, are by weight.

EXAMPLES

Example 1: Polymers B-L for Use in the Compositions of the Invention and Comparative Polymer a The polymers, designated Polymers B-L, for use in the compositions of the invention were prepared in accordance with formula 1. The details of Polymers A-L are given in Table 1 below, where the amount of AMPS is expressed over and above the combination of the other ingredients, in line with convention.

TABLE 1

Structural Composition of Polymers A-L

Hydrophobe Chain Length (n) when conforming to the structure

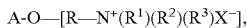

| Sample No. | Hydrophobe % | m = 23 | Ethyl Acrylate % | Methacrylic acid % | AMPS % |
|---|---|---|---|---|---|
| A | 9 | 12 | 59.5 | 31.5 | 0.25 |
| B | 9 | 12 | 59.5 | 31.5 | 0.5 |
| C | 9 | 12 | 59.5 | 31.5 | 0.75 |
| D | 9 | 12 | 59.5 | 31.5 | 1 |
| E | 9 | 12 | 59.5 | 31.5 | 1.25 |
| F | 9 | 12 | 59.5 | 31.5 | 1.5 |
| G | 16 | 12 | 52.5 | 31.5 | 1 |
| H | 20 | 12 | 48.5 | 31.5 | 1 |
| I | 16 | 13% 12, 3% 18 | 52.5 | 31.5 | 1 |
| J | 16 | 13% 18, 3% 22 | 52.5 | 31.5 | 1 |
| K | 16 | 8% 12, 8% 18 | 52.5 | 31.5 | 1 |
| L | 16 | 18 | 52.5 | 31.5 | 1 |

Polymers A-L were Made Using the Following General Preparation Method:

A 3 liter, 4 necked round bottom flask equipped with a mechanical stirrer, thermocouple, condenser and nitrogen sparge was charged with 430 g of deionized water and 4.7 g of sodium lauryl sulfate. The flask was then purged with nitrogen and its contents were warmed to 90° C. Then a first initiator solution containing 0.33 g of ammonium persulfate dissolved in 10 g of deionized water was added to the flask. Then a monomer solution was gradually charged to the flask over a period of 107 minutes, wherein the monomer solution contained 633 g deionized water, 18 g of sodium lauryl sulfate and the amounts (as noted in TABLE 1) of each of ethyl acrylate (EA), methacrylic acid (MAA), 2-acrylamido-2-methylpropane sulfonic acid (AMPS) and a lipophilically modified monomer (LIPO) having the following structure:

$$R^1\text{---}(OCH_2CH_2)_n\text{---}O\text{---}\overset{O}{\underset{R^2}{\text{C}}}\text{---}CH_2$$

wherein $R^1$ was a linear saturated $C_{12-14}$ alkyl group; $R^2$ is selected from hydrogen or methyl(preferably, wherein $R^2$ is a methyl group); and n was an average of 20 to 28. Starting simultaneously with the monomer solution charge, a second initiator solution containing 0.33 g of ammonium sulfate in 49 g of deionized water was gradually charged to the flask over a period of 112 minutes. Following the monomer charge and the second initiator solution charge, the transfer lines were rinsed with deionized water followed by a free radical catalyst and activator chase solution. The resulting latex products were recovered.

Example 2: Preparation of Shampoos S1-S20, in Accordance with the Invention and Comparative Shampoos, SA-SC Shampoos in accordance with the invention comprised Polymers B-L, whilst and comparative shampoos comprised Carbopol and Polymer A.

Comparative shampoos SA and SC were prepared by the following method:
1. The Carbomer was thoroughly dispersed in water.
3. The cleansing surfactants, cationic polymer, mica, fragrance and preservatives were then added to the Carbomer and fully dispersed.
4. The resulting formulation was adjusted to the desired pH and viscosity using suitable pH and viscosity modifiers.

Shampoos in accordance with the invention and comparative shampoo SB were prepared by the following method:
1. Polymer (Polymer (A)-(L)) was added to water.
2. The polymer was then allowed to swell by increasing the pH, using a suitable pH modifier, until a clear solution was obtained.
3. The cleansing surfactants, cationic polymer, mica, fragrance and preservatives were then added to the swollen polymer and fully dispersed.
4. The resulting formulation was adjusted to the desired pH and viscosity using suitable pH and viscosity modifiers.

The compositions are shown in the following tables.

Example 3: Analytical Methods

The following analytical methods were used in these examples:
Silicone Deposition:
Virgin hair switches were treated with the shampoo of interest. Switches were rinsed and dried before the level of silicone was quantified using x-ray fluorescence (XRF)
Thermal Stability:
Thermal stability was tested by placing the shampoo compositions in an oven at 45° C. for 12 weeks. The compositions were then assessed at regular time intervals over the 12 week period for sedimentation of mica particles.
Viscosity:
Viscosity was measured using a Brookfield RV5 spindle, at 20 rpm at 30° C.
pH:
pH was measured using a calibrated pH meter (pH was 4.5 unless otherwise stated)
Transmission:
Transmission measurements were performed on a base composition comprising 12% Sodium Laureth Sulphate, 1.6% Cocoamidopropyl Betaine and the named Polymer, that had been adjusted to neutral pH using a pH modifier. Transmission of the resulting solution was measured using a Turbiscan or similar.

Example 4: Impact of Polymer AMPS Level on Deposition of Silicone and Thermal Stability of Shampoo Shampoos were prepared, in accordance with the invention (designated S1-S5) which comprised polymers (B)-(F), having increasing amounts of AMPs (as detailed in Table 1). A Comparative Shampoo, SA, was also made, which comprised a Carbomer structurant and Comparative Shampoo SB which comprised Polymer A

TABLE 2

Compositions of Shampoos S1-S5, in accordance with the invention and Comparative Shampoo SA and SB

| INCI Name | SA % w/w | SB % w/w | S1 % w/w | S2 % w/w | S3 % w/w | S4 % w/w | S5 % w/w |
| --- | --- | --- | --- | --- | --- | --- | --- |
| Aqua | To 100% | To 100% | To 100% | To 100% | To 100% | To 100% | To 100% |
| Carbomer | 0.40 | 0.00 | 0.00 | 0.00 | 0.00 | 0.00 | 0.00 |
| Acrylate/palmeth-25 acrylates copolymer (polymer composition reference) | 0 | 0.4 (A) | 0.4 (B) | 0.4 (C) | 0.4 (D) | 0.4 (E) | 0.4 (F) |
| Sodium Laureth Sulphate | 12 | 12 | 12 | 12 | 12 | 12 | 12 |
| Titanium Dioxide (Mica) | 0.20 | 0.20 | 0.20 | 0.20 | 0.20 | 0.20 | 0.20 |

TABLE 2-continued

Compositions of Shampoos S1-S5, in accordance with the invention and Comparative Shampoo SA and SB

| INCI Name | SA % w/w | SB % w/w | S1 % w/w | S2 % w/w | S3 % w/w | S4 % w/w | S5 % w/w |
|---|---|---|---|---|---|---|---|
| Cocamidopropyl Betaine | 1.6 | 1.6 | 1.6 | 1.6 | 1.6 | 1.6 | 1.6 |
| Fragrance | 0.70 | 0.70 | 0.70 | 0.70 | 0.70 | 0.70 | 0.70 |
| Guar Hydroxypropyltrimonium Chloride | 0.20 | 0.20 | 0.20 | 0.20 | 0.20 | 0.20 | 0.20 |
| Preservatives | 0.55 | 0.55 | 0.55 | 0.55 | 0.55 | 0.55 | 0.55 |
| Viscosity modifiers | 0.75 | 0.75 | 0.75 | 0.75 | 0.75 | 0.75 | 0.75 |
| pH modifiers | 0.2 | 0.62 | 0.62 | 0.62 | 0.62 | 0.62 | 0.62 |
| Dimethicone (particle size < 10 μm) | 1.5 | 1.5 | 1.5 | 1.5 | 1.5 | 1.5 | 1.5 |

TABLE 2A

Impact of AMPS Level on deposition of silicone and thermal stability

| Silicone deposition (ppm) (+/−standard deviation) | 1361 ± 276 | −6 ± 35 | 415 ± 110 | 377 ± 124 | 465 ± 69 | 904 ± 108 | 373 ± 158 |
|---|---|---|---|---|---|---|---|
| Thermal storage stability at 45° C. (weeks) | 8-12 | >12 | >12 | 8-12 | 8-12 | 4-8 | 4-8 |

It will be seen that as the amount of AMPS increases across shampoo 1 to shampoo 5, the amount of silicone deposition peaks at shampoo 4, which has a level of 1.25% AMPS. It will also be seen that the stability of the formulation decreases as the amount of AMPS increases, therefore the AMPS level may be tailored to achieve the right balance of silicone deposition and stability for the desired application.

Example 5: Impact of Polymer Composition on Deposition of Silicone, Transmission and Thermal Stability of Shampoo Shampoos were prepared, in accordance with the invention (designated S6-S12) which comprised polymers (D) and (G)-(L), having different structural compositions (as detailed in Table 1).

Comparative Shampoo, SA, was also made, which comprised a Carbomer polymer. Transmission measurements were performed on base compositions comprising 12% Sodium Laureth Sulphate, 1.6% Cocoamidopropyl Betaine and Polymers D, G-L and Carbomer, that were adjusted to neutral pH using a pH modifier.

TABLE 3

Compositions of Shampoos S6-S12, in accordance with the invention and Comparative Shampoo SA

| INCI Name | SA % w/w | S6 % w/w | S7 % w/w | S8 % w/w |
|---|---|---|---|---|
| Aqua | To 100% | To 100% | To 100% | To 100% |
| Carbomer | 0.40 | 0.00 | 0.00 | 0.00 |
| Acrylate/palmeth-25 acrylates copolymer (polymer composition reference) | 0 | 0.4 (D) | 0.4 (G) | 0.4 (H) |
| Sodium Laureth Sulphate | 10 | 10 | 10 | 10 |
| Titanium Dioxide (Mica) | 0.20 | 0.20 | 0.20 | 0.20 |
| Cocamidopropyl Betaine | 1.5 | 1.5 | 1.5 | 1.5 |
| Fragrance | 0.70 | 0.70 | 0.70 | 0.70 |
| Guar Hydroxypropyl-trimonium Chloride | 0.20 | 0.20 | 0.20 | 0.20 |
| Preservatives | 0.55 | 0.55 | 0.55 | 0.55 |
| Viscosity modifiers | 0.75 | 0.75 | 0.75 | 0.75 |
| pH modifiers | 0.2 | 0.62 | 0.62 | 0.62 |
| Dimethicone (particle size <10 μm) | 0.75 | 0.75 | 0.75 | 0.75 |

TABLE 3A

Impact of Polymer Composition on deposition of silicone and thermal stability

| | SA | S6 | S7 | S8 |
|---|---|---|---|---|
| Silicone deposition (ppm) (+/−standard deviation) | 961 ± 192 | 319 ± 135 | 367 ± 97 | 464 ± 113 |
| Thermal storage stability at 45° C. (weeks) | 12 | 4-8 | 4-8 | 4-8 |
| % Transmission of base composition | 1.4 | 72.6 | 77.6 | 70.3 |

TABLE 4

Compositions of Shampoos S9-S12, in accordance with the invention and Comparative Shampoo SA

| INCI Name | SA % w/w | S9 % w/w | S10 % w/w | S11 % w/w | S12 % w/w |
|---|---|---|---|---|---|
| Aqua | To 100% | To 100% | To 100% | To 100% | To 100% |
| Carbomer | 0.40 | 0.00 | 0.00 | 0.00 | 0.00 |
| Acrylate/palmeth-25 acrylates copolymer | 0 | 0.4 (I) | 0.4 (J) | 0.4 (K) | 0.4 (L) |

TABLE 4-continued

Compositions of Shampoos S9-S12, in accordance with the invention and Comparative Shampoo SA

| INCI Name | SA % w/w | S9 % w/w | S10 % w/w | S11 % w/w | S12 % w/w |
|---|---|---|---|---|---|
| (polymer composition reference) | | | | | |
| Sodium Laureth Sulphate | 10 | 10 | 10 | 10 | 10 |
| Titanium Dioxide (Mica) | 0.20 | 0.20 | 0.20 | 0.20 | 0.20 |
| Cocamidopropyl Betaine | 1.5 | 1.5 | 1.5 | 1.5 | 1.5 |
| Fragrance | 0.70 | 0.70 | 0.70 | 0.70 | 0.70 |
| Guar Hydroxypropyl-trimonium Chloride | 0.20 | 0.20 | 0.20 | 0.20 | 0.20 |
| Preservatives | 0.55 | 0.55 | 0.55 | 0.55 | 0.55 |
| Viscosity modifiers | 0.75 | 0.75 | 0.75 | 0.75 | 0.75 |
| pH modifiers | 0.2 | 0.62 | 0.62 | 0.62 | 0.62 |
| Dimethicone (particle size <10 μm) | 0.75 | 0.75 | 0.75 | 0.75 | 0.75 |

TABLE 4A

Impact of Polymer Composition on deposition of silicone and thermal stability

| | | | | | |
|---|---|---|---|---|---|
| Silicone deposition (ppm) (+/−standard deviation) | 961 ± 192 | 447 ± 183 | 321 ± 91 | 396 ± 105 | 325 ± 46 |
| Thermal storage stability at 45° C. (weeks) | 12 | 8-12 | 8-12 | 8-12 | 8-12 |
| % Transmission of base composition | 1.4 | 77.1 | 66.6 | 74.6 | 58.4 |

D, G, H are polymers with increasing levels of hydrophobe. It will be seen that the silicone deposition increases as the hydrophobe level increases across S6 to S8.

I, J and K are polymers with mixed chain length hydrophobe chains. It will be seen that shampoos with mixed hydrophobe chain lengths, S9-S11, show improved silicone deposition performance, especially those containing a mixture of C12 and C18 hydrophobes (polymers I and K in S9 and S11, respectively) compared to when only a single chain length hydrophobe was used (polymers D and L, in S8 and S12, respectively).

Additionally, it will be seen that the polymers in accordance with the present invention offer greater transmission than the carbomer in the base composition. We have found that greater transmission in a base is indicative of greater quality of appearance in the end shampoo product. The impact of the high transparency has a positive visual effect even when the insoluble ingredients are present in the composition. Whilst not transparent, the shampoo compositions comprising Polymers D and G-L have an improved visual appearance.

Additionally, it will be seen the shampoos in accordance with the present invention provide a good balance of acceptable thermal stability, appearance (transmission) and silicone deposition, which is not offered by the Comparative Shampoo SA, where transmission is unacceptably low.

Example 6: Impact of SLES Ethoxylation

Shampoos in accordance with the invention, S13-S16, were prepared using the Polymer (D) as given in Table 1, and the method described in Example 2.

Comparative Shampoo, SC, was also made, which comprised a Carbomer structurant.

Target viscosity specification: 4000-7000 cP (Brookfield RV5 spindle, 20 rpm 30° C.) Target pH: 4.5 (calibrated pH meter)

TABLE 5

Compositions of Shampoos S13-S16, in accordance with the invention and Comparative Shampoo SC

| INCI Name | SC % w/w | S13 % w/w | S14 % w/w | S15 % w/w | S16 % w/w |
|---|---|---|---|---|---|
| Aqua | To 100% | To 100% | To 100% | To 100% | To 100% |
| Carbomer | 0.40 | 0.00 | 0.00 | 0.00 | 0.00 |
| Acrylate/palmeth-25 acrylates copolymer | 0 | 0.4 | 0.4 | 0.4 | 0.4 |
| Sodium Laureth Sulphate (average no. of ethoxylation units = 1) | 10 | 10 | 0 | 0 | 0 |
| Sodium Laureth Sulphate (average no. of ethoxylation units = 2) | 0 | 0 | 10 | 0 | 0 |
| Sodium Laureth Sulphate (average no. of ethoxylation units = 3) | 0 | 0 | 0 | 10 | 10 |
| Titanium Dioxide (Mica) | 0.20 | 0.20 | 0.20 | 0.20 | 0.20 |
| Cocamidopropyl Betaine | 1.5 | 1.5 | 1.5 | 1.5 | 1.5 |
| Fragrance | 0.70 | 0.70 | 0.70 | 0.70 | 0.70 |
| Guar Hydroxypropyltrimonium Chloride | 0.20 | 0.20 | 0.20 | 0.20 | 0 |
| Hydroxyethyl Cellulose | 0 | 0 | 0 | 0 | 0.20 |
| Preservatives | 0.55 | 0.55 | 0.55 | 0.55 | 0.55 |
| Viscosity modifiers | 0.75 | 0.75 | 0.75 | 0.75 | 0.75 |
| pH modifiers | 0.2 | 0.62 | 0.62 | 0.62 | 0.2 |

TABLE 5A

Impact of SLES Ethoxylation on Silicone Deposition

| | | | | | |
|---|---|---|---|---|---|
| Dimethicone (particle size <10 μm) | 1.5 | 1.5 | 1.5 | 1.5 | 1.5 |
| Silicone deposition (ppm) (+/−standard deviation) | 1629 ± 223 | 304 ± 74 | 612 ± 47 | 760 ± 219 | 919 ± 191 |

It will be seen that increased levels of SLES ethoxylation give an increased level of silicone deposition with Polymer D. (Note: SC (comprising carbomer) is known to give high amount of silicone deposition. However, the appearance is of less good quality—see Table 3A).

Example 7: Impact of Shampoo pH

Shampoos in accordance with the invention, S17-S20, were prepared using the Polymer (D) as given in Table 1, and the method described in Example 2.

TABLE 6

Compositions of Shampoos S17-S20, in accordance with the invention

| INCI Name | S17 % w/w | S18 % w/w | S19 % w/w | S20 % w/w |
|---|---|---|---|---|
| Aqua | To 100% | To 100% | To 100% | To 100% |
| Acrylate/palmeth-25 acrylates copolymer | 0.4 | 0.4 | 0.4 | 0.4 |
| Sodium Laureth Sulphate | 10 | 10 | 10 | 10 |
| Titanium Dioxide (Mica) | 0.20 | 0.20 | 0.20 | 0.20 |
| Cocamidopropyl Betaine | 1.5 | 1.5 | 1.5 | 1.5 |
| Fragrance | 0.70 | 0.70 | 0.70 | 0.70 |
| Guar Hydroxypropyl-trimonium Chloride | 0.20 | 0.20 | 0.20 | 0.20 |
| Preservatives | 0.55 | 0.55 | 0.55 | 0.55 |
| Viscosity modifiers | 0.75 | 0.75 | 0.75 | 0.75 |
| pH modifiers | 0.62 | 0.62 | 0.62 | 0.62 |

TABLE 6-continued

Compositions of Shampoos S17-S20,
in accordance with the invention

| INCI Name | S17 % w/w | S18 % w/w | S19 % w/w | S20 % w/w |
|---|---|---|---|---|
| Dimethicone (particle size <10 μm) | 0.75 | 0.75 | 1.5 | 1.5 |

TABLE 6A

Impact of shampoo pH on silicone deposition

| Shampoo pH | 4.5 | 6.5 | 4.5 | 6.5 |
|---|---|---|---|---|
| Silicone deposition (ppm) (+/−standard deviation) | 107 ± 21 | 637 ± 54 | 132 ± 16 | 1247 ± 181 |

It will be seen that pH 6.5 was beneficial.

Example 8: Impact of Polymer Crosslinking on Transmission of Shampoo Base

In a separate experiment, simple shampoo bases were prepared in accordance with the method described in Example 3 for measuring transmission. Mixture T1 was prepared according to the method containing 0.4% of the linear Polymer D, according to the invention, as described in Table 1. Comparative mixture TC was prepared via the same method and at the same active inclusion level (0.4%) with a commercially available cross-linked polymer, Carbopol Aqua SF2 supplied by Lubrizol. The measured transmission of the samples is provided in Table 7.

TABLE 7

Transmission measurements of Shampoo Mixture T1, in accordance with the invention and comparative Shampoo Mixture TC

| | Shampoo Mixture T1 | Shampoo Mixture TC |
|---|---|---|
| % Transmission of shampoo mixture | 89% | 77% |

The transmission of the composition with the linear polymer according to the present invention is higher than the commercially available cross-linked polymer.

The invention claimed is:

1. An acidic aqueous shampoo composition, which comprises:
(I) a cleansing surfactant selected from the group consisting of anionic surfactant, zwitterionic or amphoteric surfactant, nonionic surfactant, and mixtures of any thereof;
(II) an emulsified silicone;
(III) an anti-settling, thickening polymer;
wherein the anti-settling, thickening polymer, comprises:
(a) 40 to 74.5 wt % of structural units of $C_{1-4}$ alkyl acrylate;
(b) 20 to 50 wt % of structural units of methacrylic acid;
(c) 0.3 to <5 wt % of structural units of 2-acrylamido-2-methylpropane sulfonic acid (AMPS);
(d) 5 to 25 wt % of structural units of a specialized associated monomer having the following structure:

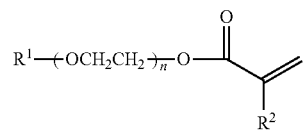

wherein $R^1$ is a linear saturated $C_{10-24}$ alkyl group; wherein $R^2$ is a hydrogen or a methyl group; and wherein n is an average of 20 to 28; with the proviso that the structural units of the specialized associated monomer (d) are derived from one of (i) a single specialized associated monomer; (ii) two specialized associated monomers, wherein $R^1$ is, respectively, a linear saturated $C_{12}$ and a linear saturated $C_{18}$ alkyl group; or (iii) two specialized associated monomers, wherein $R^1$ is, respectively, a linear saturated $C_{18}$ alkyl group and a linear saturated $C_{22}$ alkyl group;
(e) 0 to 1 wt % of structural units of acrylic acid; and
(f) 0 to 2 wt % of structural units of multi-ethylenically unsaturated crosslinking monomer and/or chain transfer agent; and
wherein the sum of the weight percentages of structural units (a)-(f) is equal to 100 wt % of the anti-settling, thickening polymer.

2. The acidic aqueous shampoo composition as claimed in claim 1, wherein the anti-settling, thickening polymer includes less than 0.001 wt % of structural units of multi-ethylenically unsaturated crosslinking monomer; and wherein the anti-settling, thickening polymer includes less than 0.1 wt % of structural units of chain transfer agent.

3. The acidic aqueous shampoo composition as claimed in claim 1, wherein the anti-settling, thickening polymer has a weight average molecular weight of 25,000,000 to 300,000,000 Daltons.

4. The acidic aqueous shampoo composition as claimed in claim 1, wherein the anti-settling, thickening polymer comprises a level of AMPS of 0.5 to 3 wt %, by total weight of the polymer.

5. The acidic aqueous shampoo composition as claimed in claim 1, wherein the anti-settling, thickening polymer includes:
(a) 50 to 65 wt % of structural units of $C_{1-4}$ alkyl acrylate, wherein the $C_{1-4}$ alkyl acrylate is ethyl acrylate;
(b) 25 to 40 wt % of structural units of methacrylic acid;
(c) 0.5 to 1.5 wt % of structural units of 2-acrylamido-2-methylpropane sulfonic acid (AMPS);
(d) 10 to 20 wt % of structural units of the specialized associated monomer;
(e) 0 to 0.1 wt % of structural units of acrylic acid; and
(f) 0 to 0.001 wt % of structural units of multi-ethylenically unsaturated crosslinking monomer or chain transfer agent.

6. The acidic aqueous shampoo composition as claimed in claim 1, which has a pH of 3 to <7.

7. The acidic aqueous shampoo composition as claimed in claim 1, wherein the emulsified silicone is selected from the group consisting of polydiorganosiloxanes, silicone gums, amino functional silicones and mixtures thereof.

8. The acidic aqueous shampoo composition as claimed in claim 1, wherein the silicone is present in an amount of from 0.01 wt % to 10% wt of the total composition.

9. The acidic aqueous shampoo composition as claimed in claim 1, wherein the cleansing surfactant is selected from the group consisting of sodium lauryl sulphate, sodium lauryl ether sulphate, sodium lauryl ether sulphosuccinate, ammonium lauryl sulphate, ammonium lauryl ether sulphate, sodium cocoyl isethionate and lauryl ether carboxylic acid, coco betaine, cocamidopropyl betaine, sodium cocoamphoacetate and mixtures thereof.

10. The acidic aqueous shampoo composition as claimed in claim 1, wherein the anionic cleansing surfactant is selected from the group consisting of sodium lauryl sulphate, sodium lauryl ether sulphate (n)EO, (where n is from 1 to 3), ammonium lauryl sulphate, ammonium lauryl ether sulphate (n)EO, (where n is from 1 to 3) and mixtures thereof.

11. The acidic aqueous shampoo composition as claimed in claim 1, wherein the mixtures of any of the anionic, non-ionic and amphoteric cleansing surfactants has a ratio of primary to secondary surfactant of between 1:1-10:1, based on the inclusion weight of the cleansing surfactant in the shampoo composition.

12. The acidic aqueous shampoo composition as claimed in claim 1, wherein the cleansing surfactant is present in an amount of from 2 to 40 wt %.

13. The acidic aqueous shampoo composition as claimed in claim 1, which further comprises a pearlescer, preferably selected from the group consisting of mica, titanium dioxide, titanium dioxide coated mica, ethylene glycol distearate and mixtures thereof.

14. A method of treating hair comprising the step of applying to the hair a composition as defined by claim 1.

15. The method as claimed in claim 14 which comprises the additional step of rinsing the hair with water.

16. The acidic aqueous shampoo composition of claim 1, wherein $R^2$ is a methyl group.

17. The acidic aqueous shampoo composition of claim 1, wherein the structural units of the specialized associated monomer (d) are derived from (i) the single specialized associated monomer wherein $R^1$ is selected from the group consisting of a linear saturated $C_{12}$ alkyl group, a linear saturated $C_{18}$ alkyl group and a linear saturated $C_{22}$ alkyl group.

18. The acidic aqueous shampoo composition of claim 1, wherein the structural units of the specialized associated monomer (d) are derived from (i) the single specialized associated monomer wherein $R^1$ is selected from the group consisting of a linear saturated $C_{12}$ alkyl group and a linear saturated $C_{18}$ alkyl group.

19. The acidic aqueous shampoo composition as claimed in claim 1, wherein the silicone is present in an amount of from 0.1 wt % to 5 wt % of the total composition.

20. The acidic aqueous shampoo composition as claimed in claim 1,
wherein the silicone is present in an amount of from 0.5 wt % to 3 wt % of the total composition.

* * * * *